United States Patent
Sankai

(10) Patent No.: US 11,103,182 B2
(45) Date of Patent: Aug. 31, 2021

(54) WALKING TRAINING SYSTEM AND WALKING TRAINING MACHINE

(71) Applicants: CYBERDYNE INC., Tsukuba (JP); UNIVERSITY OF TSUKUBA, Tsukuba (JP)

(72) Inventor: Yoshiyuki Sankai, Tsukuba (JP)

(73) Assignees: CYBERDYNE INC., Tsukuba (JP); UNIVERSITY OF TSUKUBA, Tsukuba (JP)

( * ) Notice: Subject to any disclaimer, the term of this patent is extended or adjusted under 35 U.S.C. 154(b) by 58 days.

(21) Appl. No.: 16/063,665

(22) PCT Filed: Dec. 16, 2016

(86) PCT No.: PCT/JP2016/087687
§ 371 (c)(1),
(2) Date: Jun. 18, 2018

(87) PCT Pub. No.: WO2017/104847
PCT Pub. Date: Jun. 22, 2017

(65) Prior Publication Data
US 2020/0268308 A1   Aug. 27, 2020

(30) Foreign Application Priority Data
Dec. 18, 2015   (JP) .............................. JP2015-248044

(51) Int. Cl.
*A61B 5/00*   (2006.01)
*G16H 20/30*   (2018.01)
(Continued)

(52) U.S. Cl.
CPC ............ *A61B 5/486* (2013.01); *A61B 5/1038* (2013.01); *A61B 5/6829* (2013.01); *A61B 5/742* (2013.01);
(Continued)

(58) Field of Classification Search
CPC ..... A61B 5/486; A61B 5/1038; A61B 5/6829; A61B 2562/0219; A61B 5/742;
(Continued)

(56) References Cited

U.S. PATENT DOCUMENTS

| | | | |
|---|---|---|---|
| 2009/0079559 A1* | 3/2009 | Dishongh | A61B 5/112 340/539.13 |
| 2010/0035728 A1 | 2/2010 | Shinomiya | |
| 2014/0058299 A1* | 2/2014 | Sankai | A61H 3/00 601/35 |

FOREIGN PATENT DOCUMENTS

| JP | 2002263152 A | 9/2002 |
|---|---|---|
| JP | 2002-306628 A | 10/2002 |

(Continued)

OTHER PUBLICATIONS

International Search Report and Written Opinion for related International Application No. PCT/JP2016/087687, dated Feb. 21, 2017; English translation of ISR provided; 12 pages.
(Continued)

*Primary Examiner* — Devin B Henson
*Assistant Examiner* — Joseph A Tombers
(74) *Attorney, Agent, or Firm* — Procopio, Cory, Hargreaves & Savitch LLP

(57) ABSTRACT

A walking training system and walking training machine capable of remarkably enhancing the effect of improving an independent walking function are proposed. When a subject having a lower limb functional disorder performs walking training, the degree of dependency on upper limbs can be evaluated by enabling the subject to recognize transitional reductions of a load on a holding part(s) by feeding back the transitional reductions of the load as a sense to feel them.

5 Claims, 15 Drawing Sheets

70:Walking Training Machine

(51) Int. Cl.
*G16H 50/50* (2018.01)
*G16H 50/30* (2018.01)
*G16H 40/63* (2018.01)
*A61B 5/103* (2006.01)
*A61H 3/00* (2006.01)
*A61H 3/04* (2006.01)
*A63B 22/02* (2006.01)

(52) U.S. Cl.
CPC ............... *A61H 3/00* (2013.01); *A61H 3/04* (2013.01); *G16H 20/30* (2018.01); *G16H 40/63* (2018.01); *G16H 50/30* (2018.01); *G16H 50/50* (2018.01); *A45B 2200/05* (2013.01); *A61B 2562/0219* (2013.01); *A61H 2201/1635* (2013.01); *A63B 22/02* (2013.01)

(58) Field of Classification Search
CPC ........ G16H 50/50; G16H 50/30; G16H 20/30; G16H 40/63; A61H 3/04; A61H 3/00; A61H 2201/1635; A63B 22/02; A45B 2200/05

See application file for complete search history.

(56) References Cited

FOREIGN PATENT DOCUMENTS

| | | |
|---|---|---|
| JP | 2003-144580 A | 5/2003 |
| JP | 2015-139554 A | 8/2015 |
| WO | 2008/093406 A1 | 8/2008 |
| WO | 2012/118143 A1 | 9/2012 |

OTHER PUBLICATIONS

Extended European Search Report for related EP App No. 16875821.7 dated Jun. 28, 2019, 7 pgs.

* cited by examiner (A)

(B)

(A)

(B)

(A)

(B)

70:Walking Training Machine

WALKING TRAINING SYSTEM AND WALKING TRAINING MACHINE

CROSS-REFERENCE TO RELATED APPLICATIONS

This application is a U.S. National Stage entry of PCT Application No: PCT/JP2016/087687 filed Dec. 16, 2016, which claims priority to Japanese Patent Application No. 2015-248044, filed Dec. 18, 2015, the contents of which are incorporated herein by reference.

TECHNICAL FIELD

The present invention relates to a walking training system and a walking training machine. Particularly, the invention is suited for use as support technology for functional improvements of independent walking disability attributable to a lower limb functional disorder.

BACKGROUND ART

For example, when it is difficult to walk independently due to the lower limb functional disorder caused by disease onset, walking training is performed by holding onto a walking aid tool such as a walking training machine or a cane and supporting a body with their upper limbs' muscles (mainly their arms power). Particularly, training of walking motion is important rehabilitation related to activities of daily living (ADL: Activities of Daily Living) and improvements of the daily living can be expected by means of the walking training.

Conventionally, there has been proposed a walking training machine that includes handrails for a subject to hold onto with their both hands and wheels attached to its frame bottom. Then, the subject performs training to walk on the flat ground in the state of holding and pushing the handrails with their both hands.

When the subject who has a gait disorder performs the walking training by using such walking training machine, they generally receive instructions from a physical therapist through visual diagnosis; however, physical changes during the subjects' walking training such as shifts in the body weight, the balance between the right and the left, or differences in the strength between the right leg and the left leg cannot be judged only by receiving the instructions from the physical therapist and it has been difficult to give appropriate instructions for a more effective training method depending on each subject's individuality (such as the balance between the right and the left during walking).

In order to redeem such defects of the training method, there has been proposed a walking training, when performed by a subject, to cause a load imposed on a pair of holding parts (handrails) provided on a walking training machine to be fed back as visual information so that the subject will recognize the load and perform the training while understanding their own walking status (PTL 1).

With a feedback system which uses this visual information, the subject can recognize by themselves the dependent load on the right and left holding parts (handrails) during the walking training on a real-time basis; and as the subject becomes aware of the dependency on the right and left holding parts, they can correct the dependency, reduce the bias or the handrail depending load, and master walking with lower dependency.

CITATION LIST

Patent Literature

PTL 1: Japanese Patent Application Laid-Open (Kokai) Publication No. 2015-139554

SUMMARY OF THE INVENTION

Problems to be Solved by the Invention

Meanwhile, safe and independent walking needs to be regained in order to overcome the lower limb functional disorder and achieve reintegration into the society; and the training content of the walking training for the lower limb functional disorder can be divided according to disease stages, such as an acute stage, a recovery stage, and a maintenance stage, which make the transition from one stage to another in a phased manner.

The maintenance stage of these disease stages is a period of time reached after the elapse of approximately six months at a maximum, which varies depending on the relevant disease, after the disease onset; and during the maintenance stage, the number of handicapped persons is the largest among the disease stages and furthermore the functional recovery stagnates. Therefore, in order to solve social problems caused by the lower limb functional disorder, it is important to develop independent walking functional improvement support technology targeted at the maintenance stage.

Various evaluation methods (such as a 10-m walking test and a 2-minute walking test) and evaluation items (such as a walking speed, a cadence, a stride length, BBS [Berg Balance Scale], and a Barthel scale) have been conventionally proposed in order to evaluate the functional improvements of the lower limb functionally handicapped persons and have been utilized in the field of physical therapy.

However, walking is performed with systemically coordinated motions and it is necessary to quantitatively evaluate the body weight support by the upper limbs and the balance maintenance in order to improve the independent walking function to achieve the safe independent walking.

However, there has been a problem of difficulty in quantitatively evaluating the above-mentioned body weight support by the upper limbs and the balance maintenance by using only the conventional evaluation items.

The present invention was devised in consideration of the above-described circumstances and aims at proposing a walking training system and walking training machine capable of remarkably enhancing the effect of improving the independent walking function.

Means to Solve the Problems

In order to solve the above-described problem, provided according to the present invention is a walking training system including: a foot load measurement unit that is mounted on right and left foot sole surfaces of a subject and measures a load applied to each of the foot sole surfaces; a gravity center position detecting unit that detects a gravity center position of each of the right and left foot sole surfaces of the subject through a change in the load measured by the foot load measurement unit; a holding part that is mounted on a walking training machine for performing walking training and is held by the subject to support part of the subject's own body weight; a holding load detection unit that detects a force applied to either one or both of a vertical direction and an opposite direction in a distribution of force acting on the holding part; an evaluation index generation unit that generates an evaluation index for quantitatively reflecting transitional reductions of the force, which is applied to the holding part, on the basis of a relationship of periodically repeated increases and decreases of the force applied to the holding part and detected by the holding load detection unit in synchronization with timing to switch the load, which is applied to the gravity center position of each of the subject's right and left foot sole surfaces and detected by the gravity center position detecting unit, between right and left; and a sensory communication unit that feeds back and transmits a transmission signal according to the evaluation index as a sense to the subject.

With the above-described walking training system, the evaluation index based on a temporal relationship between the force of the subject having the lower limb functional disorder, which acts on the holding part during the walking training, and the gravity center position of each of the right and left foot sole surfaces is fed back as a sense to the subject. So, the degree of dependency on the upper limbs can be evaluated as the subject themselves recognizes the transitional reductions of the load on the holding part.

Furthermore, according to the present invention, the evaluation index generation unit generates the evaluation index by: dividing the force applied by the subject to the holding part into a relatively large state and a relatively small state with reference to a predetermined threshold value and then forming a coordinate system by setting time mean values in the respective states as orthogonal axes; and setting an origin of the coordinate system as a target value in an independent walking state and mapping the transitional reductions of the force applied to the holding part as a vector representing a degree of recovery relative to the target value by setting a current state as a starting point.

As a result, while the subject having the lower limb functional disorder receives the feedback as the sense based on this evaluation index, they can understand the progress of any improvements of the independent walking function and set a clear target to reduce the handrail reaction force and this can contribute to appropriate diagnosis based on the quantitative results and enhancement of the motivation of the subject having the lower limb functional disorder.

Furthermore, according to the present invention, the evaluation index generation unit groups a status of the subject's lower limb functional disorder according to a degree of seriousness and divides each group in the coordinate system in a phased manner so that a distance from the target value becomes shorter in proportion to magnitude of dispersion and correlation of the vector.

As a result, the subject having the lower limb functional disorder can recognize the distribution tendency of groups representing the degree of seriousness of the status of their own disorder and this can further contribute to the enhancement of the motivation for the training.

Furthermore, the present invention includes a load relieving unit that relieves part of the body weight of the subject, wherein the load relieving unit makes an adjustment to relieve only a predetermined amount, which is set with reference to the body weight of the subject, in synchronization with the timing to switch the load applied to the gravity center position of each of the subject's right and left foot sole surfaces between the right and the left.

As a result, it is possible to enhance: physical support which will not hinder the independent walking function; removal of psychological factors which cause the subject to feel anxiety when not depending on the upper limbs; and the sense feedback effect. It is possible to further amplify the effect of reducing the force applied to the holding part.

Furthermore, the present invention includes an acceleration sensor that is mounted on the right and left foot sole surfaces of the subject and detects acceleration of each foot, wherein a degree of changes in a walking pattern of the subject is detected by continuing recording a detected result of the acceleration sensor for a predetermined period of time.

As a result, whether the subject suffers from dementia or not can be judged based on the degree of changes in the subject's walking pattern over the predetermined period of time and this can contribute to not only improvements of the lower limb functional disorder, but also to early discovery of the dementia.

Advantageous Effects of the Invention

According to the present invention, when the subject having the lower limb functional disorder performs the walking training, the subject recognizes the transitional reductions of the load on the holding part while the transitional reductions of the load on the holding part are fed back as the sense. As a result, the degree of dependency on the upper limbs can be evaluated and the effect of improving the independent walking function can be enhanced remarkably.

DESCRIPTION OF EMBODIMENTS

An embodiment of the present invention will be described below in detail with reference to the drawings.

(1) First Embodiment

(1-1) Overall Configuration of Walking Training System

Figure 1:
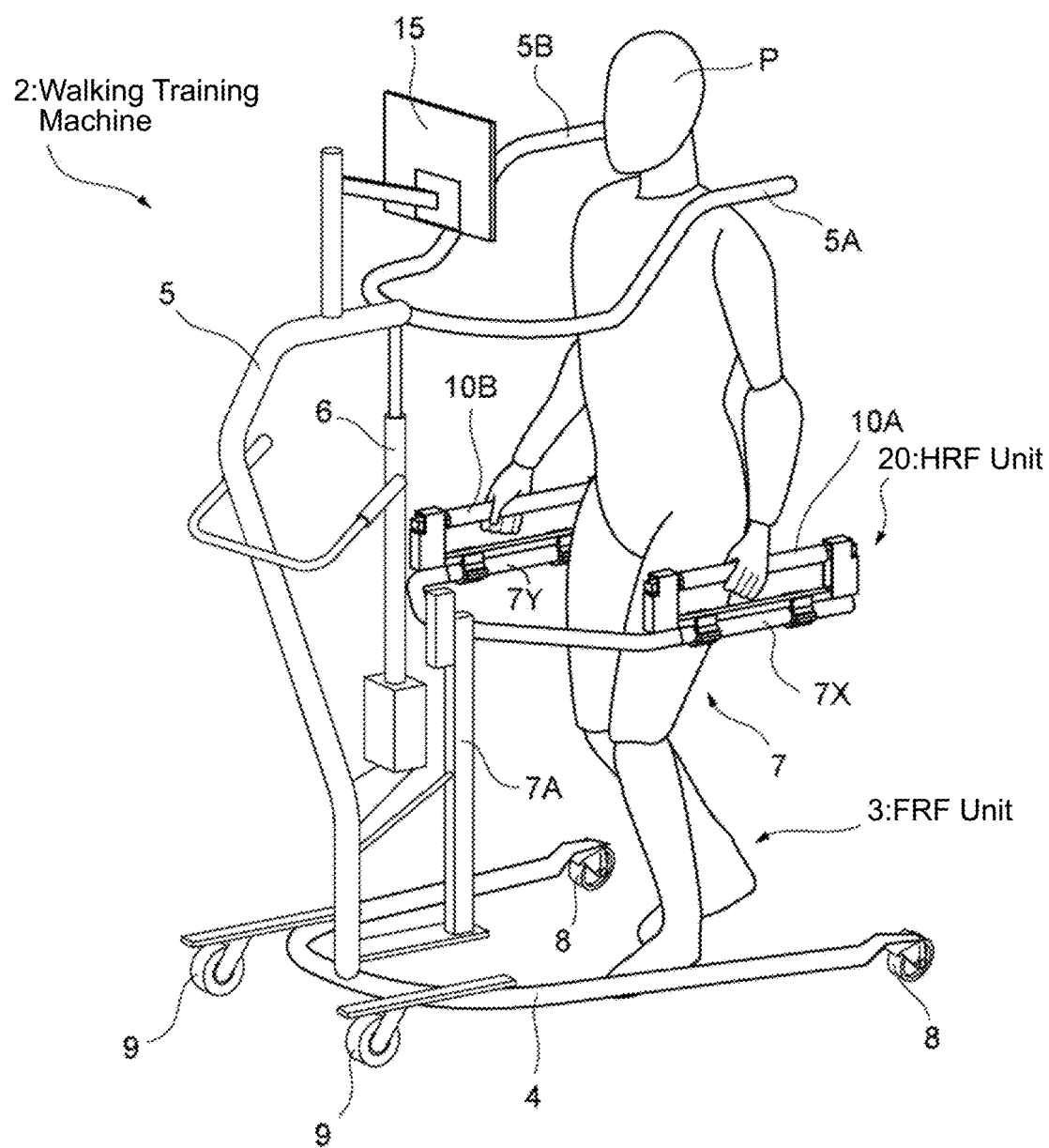
FIG. 1 is an appearance diagram illustrating an overall configuration of a walking training system according to an embodiment of the present invention.

FIG. 1 illustrates a walking training system 1 according to the present invention and is configured of: a walking training machine 2 for assisting subject P having a lower limb functional disorder with independent walking by using their upper limbs; and FRF (Floor Reaction Force [N]) units (gravity center position detecting units) 3 which are shoes to be worn on the feet of the subject P, and each of which includes a ground reaction force sensor (foot load measurement unit) mounted on each shoe sole.

The walking training machine 2 has a frame structure in which the following components are integrated: a base frame 4 that is formed in a substantially U-shape to secure a walking space for the subject P; a load relieving frame 5 that is implanted on the base frame 4 so as to make its height freely adjustable and has its top ends formed in a substantially U-shape so as to hang somewhere around the lower back part in order to prevent the subject P from falling down; and an upper limbs supporting frame 7 that is formed in a substantially U-shape to be held by the subject P with their both hands via a support pole 7A implanted on the base frame 4 so as to make its height freely adjustable.

The base frame 4 has a pair of wheels 8 mounted on both the substantially U-shaped ends and a pair of wheels 9 mounted so as to extend outward from the center of the substantially U-shaped frame; and the base frame 4 supports both the upper limbs supporting frame 7 and the load relieving frame 5 and is designed so as to be capable of moving, integrally with the upper limbs supporting frame 7 and the load relieving frame 5, in a direction desired by the subject P.

The load relieving frame 5 is structured so that a support pole 6 whose height is adjustable as a support bypass for the frame body is supported with reference to the base frame 4; and part of the body weight of the subject P is relieved by retaining the lower back part of the subject P via wires (not shown) hanged from both the substantially U-shaped ends 5A, 5B of the frame body.

The upper limbs supporting frame 7 is equipped with HRF (Handrail Reaction Force [N]) units (holding load detection units) 20, each of which includes a holding part 10A, 10B, on the right and left sides with respect to a pair of handrails 7X, 7Y extending in a U-shape in a horizontal direction from the upper end of the support pole 7A.

Furthermore, a display unit 15 and speaker (not shown), which are composed of a tablet PC equipped with a liquid crystal display, are mounted on the load relieving frame 5 so that the subject P can watch a display screen and listen to generated sounds while performing the walking training.

Each of the pair of FRF units 3 has a ground reaction force sensor (not shown) and is designed to detect the gravity center position based on balance of the load applied to the right and left foot soles of the subject P and transmit the detection result to a control system unit for the walking training machine 2 via wireless communication.

The subject P can perform the training to walk in a desired direction while holding the holding parts 10A, 10B for the pair of HRF units 20 from above with their right and left hands in a state where part of the body weight is relieved by the load relieving frame 5.

Under this circumstance, visual information based on a signal from the ground reaction force sensors for the shoe soles in the FRF units 3 mounted on both feet of the subject P and a signal from the HRF units 20 held by the subject P is displayed on the display unit 15.

(1-2) Configuration of HRF Unit

Figure 2:
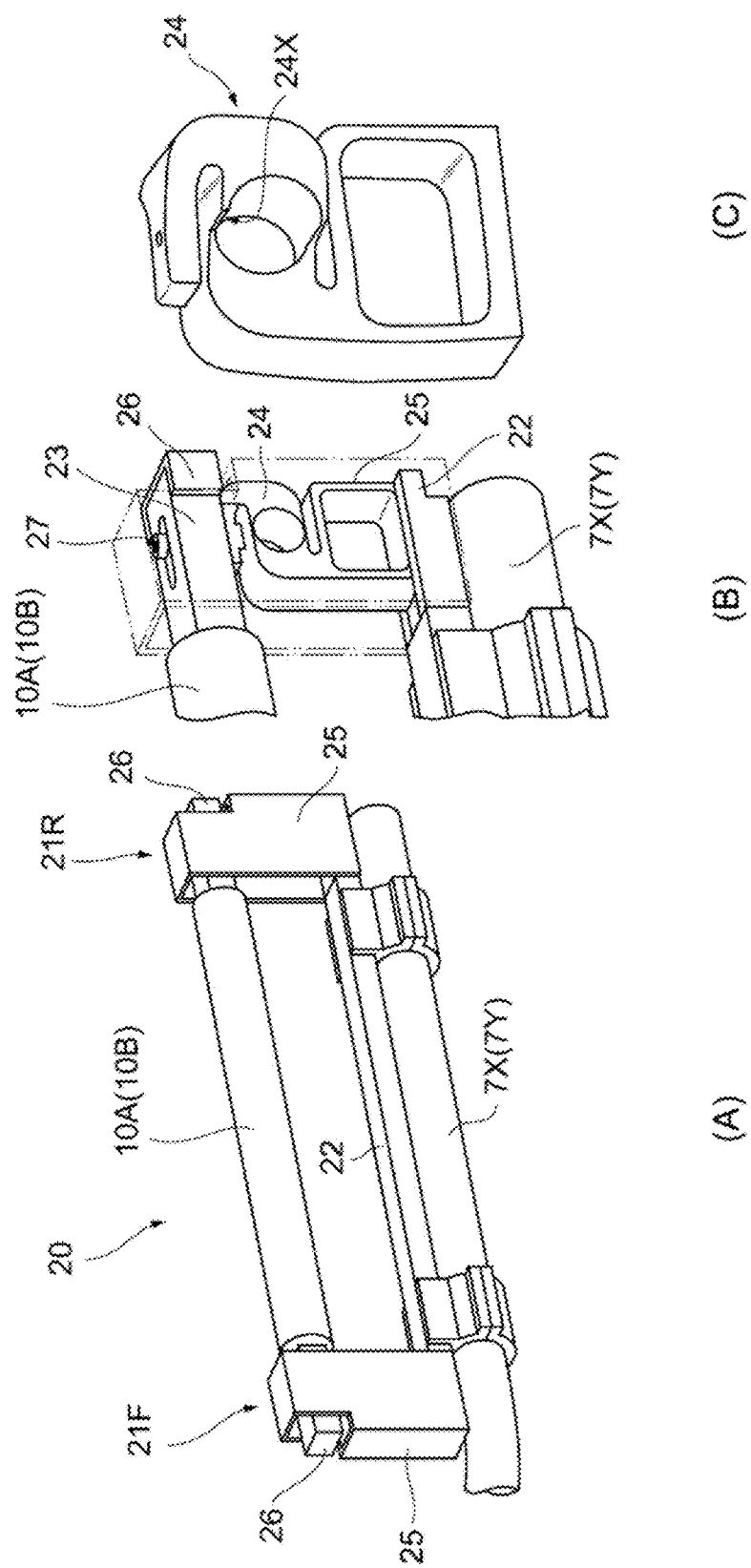
FIG. 2 is perspective views illustrating the appearance and component configuration of an HRF unit according to an embodiment of the invention.

The HRF unit 20 has a both-ends-supported structure in which both ends of the holding part 10A (10B) having a rod shape of a predetermined size are secured, via holding load detection units 21F, 21R, to the upper side of the handrail 7X (7Y) of the upper limbs supporting frame 7 integrally with a support shaft 22 as illustrated in FIG. 2A; and force applied in a vertical direction and in its opposite direction, from among a distribution of force acting on the relevant holding part 10A (10B), is measured by the holding load detection unit 21F, 21R.

This holding load detection unit 21F, 21R is secured to the handrail 7X (7Y) of the upper limbs supporting frame 7 in a state where an upper part and lower part of a mechanical force sensor 24 are in contact with, and located between, the support shaft 22 and an end 23 of the holding part 10A (10B) as illustrated in FIG. 2B. The support shaft 22, the mechanical force sensor 24, and the end 23 are placed in, and covered with, a support cover 25.

Figure 3:
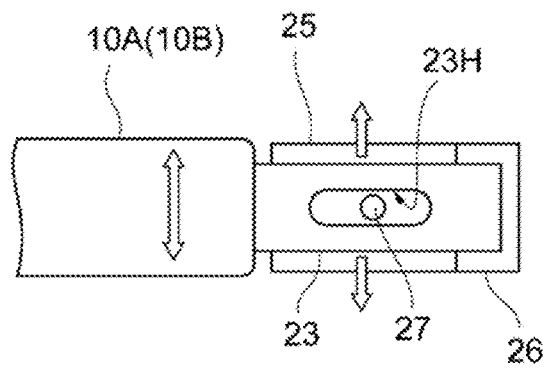
FIG. 3 is a conceptual diagram for explaining a state of transmission of force applied to a holding part for the HRF unit according to the embodiment.
Figure 3:
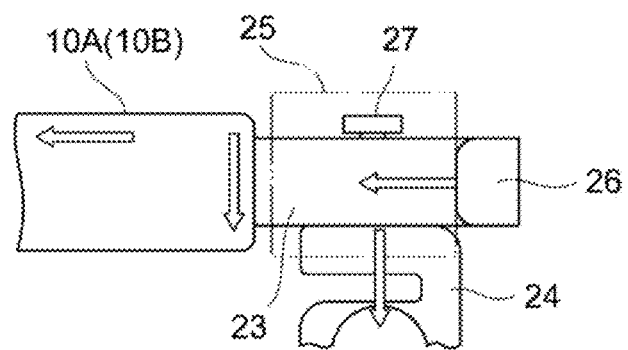

A stopper 26 is secured to, and retained at, the end 23 of the holding part 10A (10B) while in contact with the support cover 25; and a load in a front-back direction (longitudinal direction) which is transmitted to the stopper 25 is directly transmitted to the handrail 7X (7Y) via the support cover 25 (that is, without intermediary of the mechanical force sensor 24) (FIG. 2B and FIG. 3B).

Furthermore, the holding load detection unit 21F, 21R is designed to fasten a screw 27 into a long hole 23H which passes through, and is formed in, the end 23 of the holding part 10A (10B) in a vertical direction, so that a load applied to the screw 27 in a crosswise direction (horizontal direction) is directly transmitted the handrail 7X (7Y) without intermediary of the mechanical force sensor 24 (FIG. 3A).

As a result, the holding load detection unit 21F, 21R transmits the loads, which are applied to the end 23 of the holding part 10A (10B) in the front-back direction (the longitudinal direction) and in the crosswise direction (the horizontal direction), directly to the handrail 7X (7Y) via the support cover 25, while transmitting only the load applied to the end 23 of the holding part 10A (10B) in the vertical direction (the vertical direction) to the mechanical force sensor 24.

Since a material which can easily be distorted and hardly break down is desired in order to detect strain efficiently as illustrated in FIG. 2C where a displacement result is exaggerated by simulation, the mechanical force sensor 24 is formed from aluminum alloy (for example, JIS number: A7075-T6) with a relatively low Young's modulus and a relatively high yield point.

Specifically speaking, a thin part 24X is formed on the mechanical force sensor 24 within a range where a minimum safety rate relative to yield stress is 3 or more when a load corresponding to the mass of 25 kg is applied; and a surface of the thin part 24X is a strain surface. A cut shape of this thin part 24X is formed into a circular shape in order to avoid concentration of the stress.

Two strain gauges (not shown) are pasted on the surface of the thin part 24X of this mechanical force sensor 24, so that its detection sensitivity can be enhanced to twice as high as a case of either extension or compression, by measuring the stress of extension and compression at the same time.

Furthermore, the strain gauge has an internal bridge circuit constructed by a half bridge method in order to avoid drift influences caused by, for example, a temperature. For example, a uniaxial strain gauge (a foil strain gauge KFG-1N-120-C1-23 manufactured by Kyowa Electric Co.) is used, whose resistance value is 120Ω, gauge factor is 2.1, self-temperature compensated range is from 10° C. to 100° C., length is 4.2 mm, width is 1.4, and gauge length is 1 mm.

A load amount L which acts on the holding part 10A (10B) is proportionate to the sum of strain $\varepsilon f$ and strain $\varepsilon b$ which are caused to the mechanical force sensors 24 in the holding load detection units 21F, 21R on the front and rear sides. If a conversion factor C is determined as a constant in advance, the relationship of the following formula (1) is established.

[Math. 1]

$$L = C\,(\varepsilon f + \varepsilon b) \quad (1)$$

According to experiments, the load amount L which acts on the holding part 10A (10B) is measured within an average error range of approximately −1.8N to approximately 1.4N, so that a target resolution of the load measurement (approximately 2N corresponding to the mass of 200 g) can be realized.

When the subject P performs the walking training by holding the right and left holding parts 10A, 10B of the pair of HRF units 20 respectively, only the load in the vertical direction or in its opposite direction when pressing each holding part 10A, 10B can be detected. Specifically speaking, the HRF unit 20 can detect the reaction force generated in either one or both of the vertical direction and the opposite direction with respect to the load acting on the holding part 10A, 10B (hereinafter simply referred to as the "handrail reaction force") without being influenced by how and at which position the holding part 10A, 10B is held by the subject P.

(1-3) Configuration of FRF Unit

Each ground reaction force sensor 30 (FIG. 4) for the pair of FRF units 3 detects a reaction force with respect to a load applied to the right and left foot soles of the subject P. The ground reaction force sensor 30: is composed of, for example, a piezoelectric element which outputs a voltage according to the applied load, or a sensor whose electrostatic capacity changes according to the load; and can detect changes in the load caused by shifts in the body weight and whether the legs of the subject P have touched the ground or not, respectively. Also, the gravity center position can be found based on the balance of the load on the right and left foot soles.

Accordingly, the pair of FRF units 3 can estimate towards which side of the legs of the subject P, either the right leg or the left leg, the center of gravity is biased based on data measured by each ground reaction force sensor 30. Incidentally, the FRF units 3 are composed of shoes, but may be composed as insoles which can be freely attached to, or detached from, the inside of the shoes of the subject P.

(1-4) Configuration of Control System for Walking Training System

Figure 4:
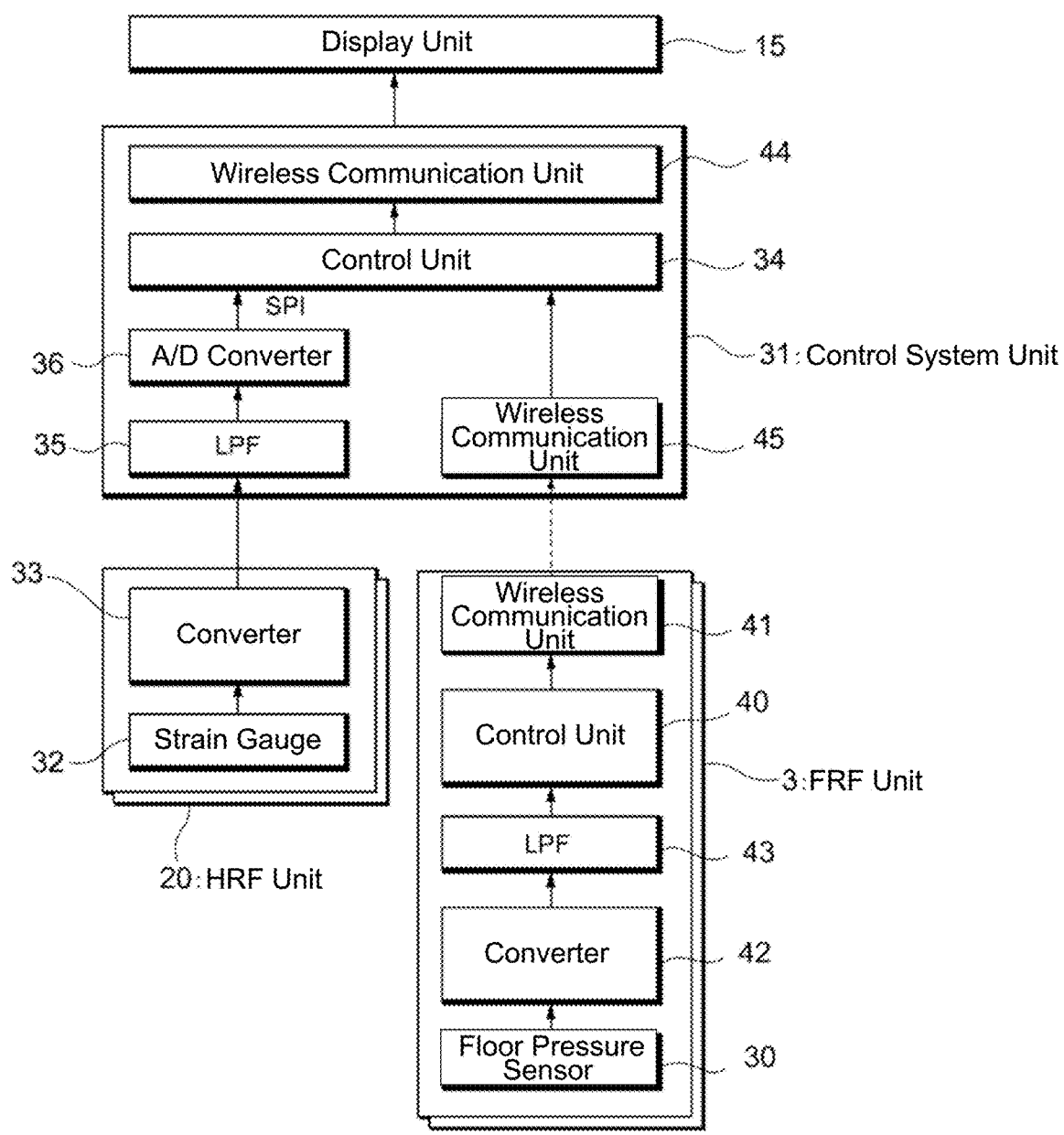
FIG. 4 is a block diagram illustrating the configuration of a control system for the walking training system according to the embodiment.

FIG. 4 is a block diagram illustrating the configuration of a control system for the walking training machine 2 and the FRF unit 3 in the walking training system 1 according to this embodiment. The walking training machine 2 includes, besides the aforementioned frame structure (the base frame 4, the upper limbs supporting frame 7, and the load relieving frame 5), a control system unit 31, the HRF units 20, the display unit 15, and a wireless communication unit 32.

The HRF unit 20 has the holding load detection unit 21F, 21R mounted on the holding part 10A, 10B secured to the handrail and detects a load amount in upward and downward directions (in a vertical direction and its opposite direction) when the subject P holds the holding part 10A, 10B with their hand. A strain amount of the thin part 24X (that is, the strain gauge 32) of the mechanical force sensor 24 which is built in the holding load detection unit 21F, 21R is converted into a voltage via a converter 33 and is transmitted as a load value signal to the control system unit 31.

The control system unit 31: includes a control unit 34 which is an MCU (Micro Control Unit); and blocks high frequency bands of the load value signal, which has been transmitted from the HRF unit 20, via an LPF (Low Pass Filter) 35 and then inputs the load value signal as HRF data, which is a chronological digital data, into the control unit 34 through an A/D converter 36.

Furthermore, the FRF unit 3 includes, besides the shoe structure, the ground reaction force sensor 30, a control unit 40 which is an MCU, and a wireless communication unit 41. After an output of the ground reaction force sensor 30 mounted on the shoe sole is converted into a voltage via a converter 42, the high frequency bands are blocked via an LPF 43 and then the obtained data is input to the control unit 40. This control unit 40 finds changes in the load caused by shifts in the body weight of the subject P and whether the feet of the subject P have touched the ground or not, based on the detected results of the ground reaction force sensor 30, and also finds the gravity center position according to the load balance between the right and left foot soles and transmits this as FRF data to the wireless communication unit 41.

The control system unit 31 receives the FRF data, which has been transmitted from the wireless communication unit 41 for the FRF unit, via the wireless communication unit 45 and then the FRF data is input to the control unit 34.

The control unit (evaluation index generation unit) 34 generates an evaluation index regarding improvements of the independent walking function by reductions of dependency of the subject P on their upper limbs and a handrail reaction force map (HRFMAP) in which the quantitative evaluation content of the evaluation index is formed into a graph as described later, based on the HRF data transmitted from the HRF units 20 and the FRF data transmitted from the FRF units 3.

Subsequently, the control unit 34 transmits evaluation data representing the evaluation index and the handrail reaction force map (HRFMAP), which have been set, via the wireless communication unit 44 to the display unit 15. The display unit 15 is composed of a tablet PC and executes processing for drawing the evaluation index and the handrail reaction force map based on the evaluation data and displays them on a display screen.

As a result, the subject P can work on the walking training while visually checking the handrail reaction force map, which is displayed on the display screen of the display unit 15, on a real-time basis as motor learning information.

With the walking training system 1 as described above, a system for a series of visual feedbacks (VF) for contributing to improvements of the walking training of the subject P can be constructed by having each detected result of the HRF units 20 and the FRF units 3 for the walking training machine 2 as visual information reflected in the senses of the subject P.

Incidentally, this embodiment has been described about the case where wireless communication is used between the control system unit 31 and the display unit 15; however, the present invention is not limited to this example and the control system unit 31 and the display unit 15 may be connected via wired communication.

(1-5) Construction of Visual Feedback System Based on Evaluation Index (1-5-1) Method for Setting Handrail Reaction Force Map (HRFMAP)

Now, an explanation will be given about a method for setting the evaluation index and the handrail reaction force map (HRFMAP) to evaluate influences exerted by the visual feedback system for the walking training system 1 according to the present invention on reductions of the handrail reaction force (HRF) of the subject P having the lower limb functional disorder.

Figure 5:
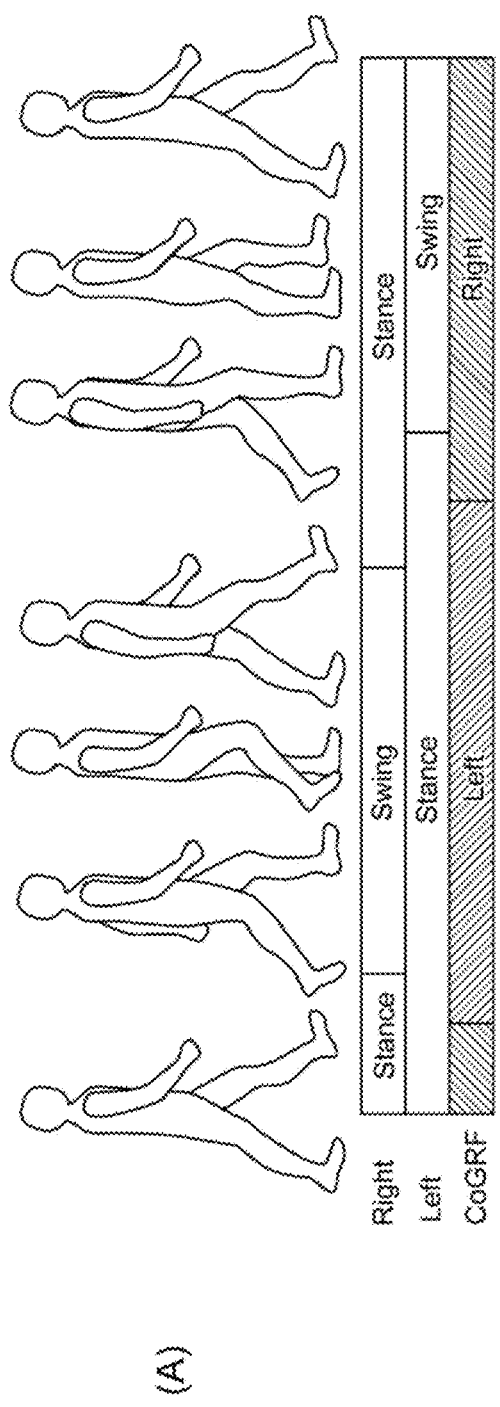
FIG. 5 is a conceptual diagram illustrating the relationship between a handrail reaction force and a walking motion position.
Figure 5:
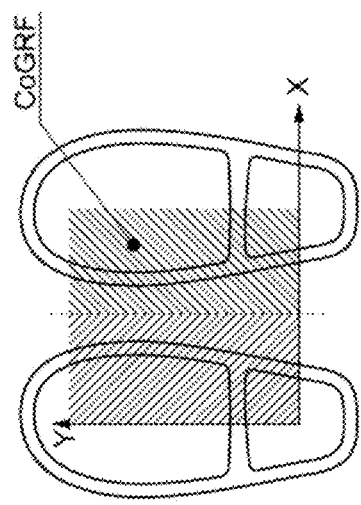

A walking cycle is mainly classified into two types as illustrated in FIG. 5A: a swing leg period (swing) when a foot sole part is off the ground; and a stance leg period (stance) when the foot sole part is in contact with the ground. Since a lower limb functionally handicapped person depends on their upper limbs to complement their lower limb function, it is estimated that the handrail reaction force may be attributed to the walking motion and change in relation to the walking cycle.

So, regarding the walking training system 1 according to the present invention, the relevance between the handrail reaction force and the walking motion is clarified and the influences exerted by the aforementioned visual feedback system on reductions of the handrail reaction force of the lower limb functionally handicapped person are evaluated.

As the subject P performed a handrail reaction force measurement experiment described below, the relevance between cycles for switching the center of ground reaction force (CoGRF: Center of Ground Reaction Force) between the right and the left and changes in the handrail reaction force was clarified. In this experiment, the handrail reaction force was measured when the subject P in the maintenance stage performed the training to walk for a predetermined distance (for example, a direct distance of 10 m).

This time, each of a spine cord injured patient (SCI), a traumatic brain injured patient (TBI), and a cerebrovascular cerebral palsy patient (CVD) as subjects P was asked to perform a 10-m walking test for more than once and the handrail reaction force and the ground reaction force within a 10-m section were measured.

Figure 6:
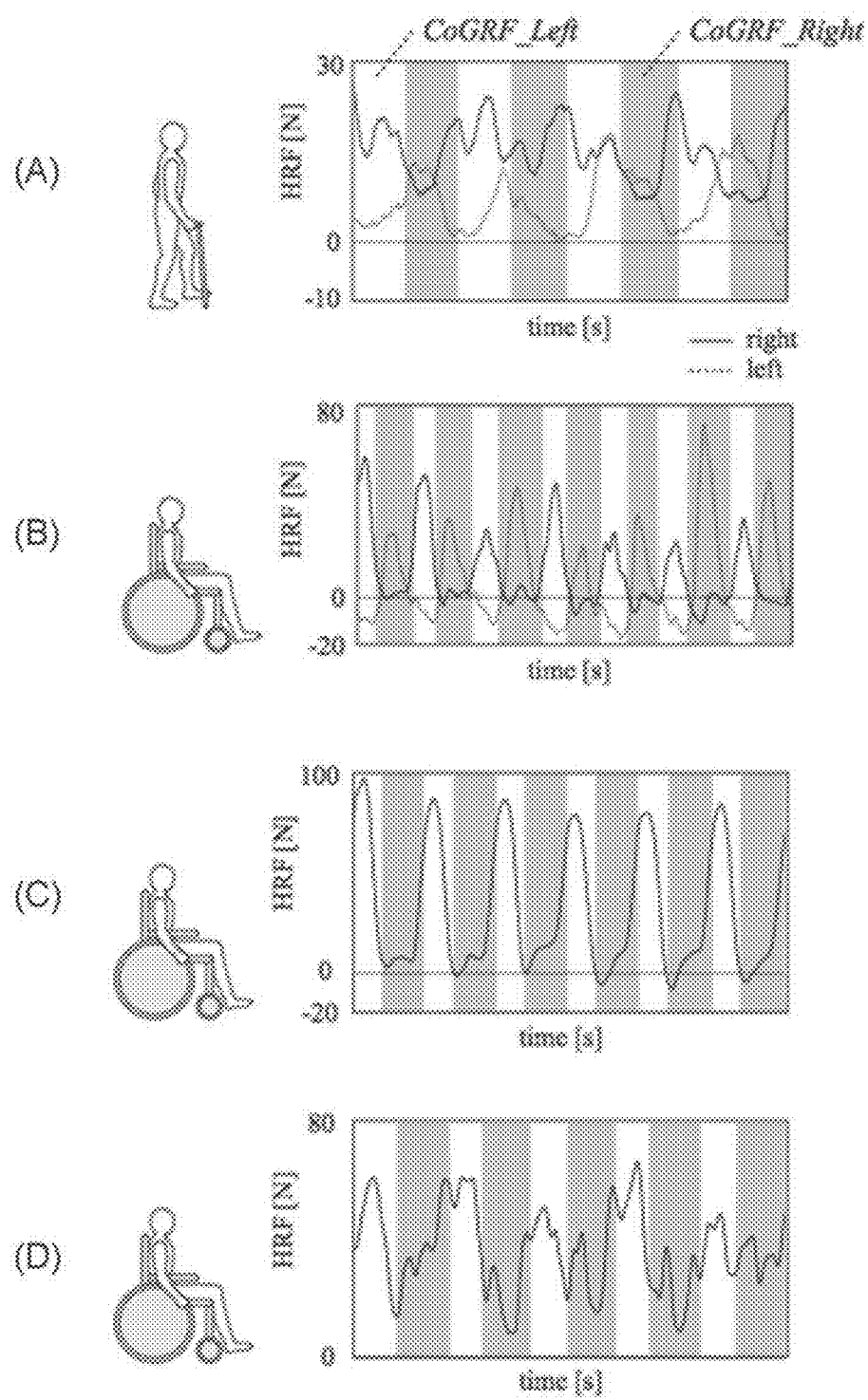
FIG. 6 is graphs showing the results of a demonstration test by walking training.

FIG. 6A to FIG. 6D show graphs representing the results of the demonstration tests of the walking training. FIG. 6A is an experiment result that chronologically shows changes in the load calculated from the handrail strain amount by the spine cord injured patient (CDI) and transitional changes in the center of ground reaction force between the right and the left. FIG. 6B is an experiment result that chronologically shows changes in the load calculated from the handrail strain amount by the traumatic brain injured patient (TBI) and transitional changes in the center of gravity on feet between the right and the left. FIG. 6C and FIG. 6D are experiment results that chronologically show changes in the load calculated from the handrail strain amount by the cerebrovascular cerebral palsy patient (CVD) and transitional changes in the center of gravity on feet between the right and the left.

The left handrail reaction force is indicated with a broken line and the right handrail reaction force with a solid line. Regarding each time series graph, a gray mask is applied to sections which are estimated as the center of gravity on the right foot based on the ground reaction force; and a white mask is applied to sections which are estimated as the center of gravity on the left foot. Incidentally, referring to FIG. 6B, part of the body weight was relieved for the subject P. Referring to FIG. 6C and FIG. 6D, the subject P had severe paralysis on their right hand and walked by using only their left hand to hold onto the walking training system, so that no solid line for the right handrail reaction force is indicated.

According to the above-described test results, it was confirmed that regarding each one of the subjects P having the lower limb functional disorder in FIG. 6A to FIG. 6D, the center of gravity on feet and the handrail reaction force are related to each other and the left-hand handrail reaction force tends to increase with the center of gravity on the right foot and the right-hand handrail reaction force tends to increase with the center of gravity on the left foot.

As a result of comparison of the cycles for switching the center of ground reaction force between the right and the left, which is calculated from time and the number of steps required by each subject P to perform the walking test for the walking distance of 10 m, with dominant frequencies of changes in the handrail load calculated based on Fourier analysis, the same degree of results was obtained with respect to all the subjects P.

As a result of the above, it was confirmed regarding the walking motion of the subject P having the lower limb functional disorder that the handrail reaction force periodically repeats increasing and decreasing in accordance with switching of the center of ground reaction force between the right and the left.

(1-5-2) Method for Calculating Evaluation Index for Handrail Reaction Force

Subsequently, the relationship between improvements of the independent walking function and reductions of the handrail reaction force will be examined based on the result of the aforementioned method for evaluating the handrail reaction force. A subject P having the lower limb functional disorder in a relatively severe condition rides a wheelchair as their daily means of mobility; and as their lower limb function improves, the subject P uses a walking training machine and a cane, and eventually regain the independent walking.

Firstly, regarding the walking training in the maintenance stage, a waveform reference for a handrail reaction force (HRF) value upon periodic increase/decrease varies between a state where the subject P having the lower limb functional disorder depends on the walking training machine or the cane to bear most of their weight during walking and a state where the subject P having the lower limb functional disorder uses the cane during walking only for the assistive purpose.

Figure 7:
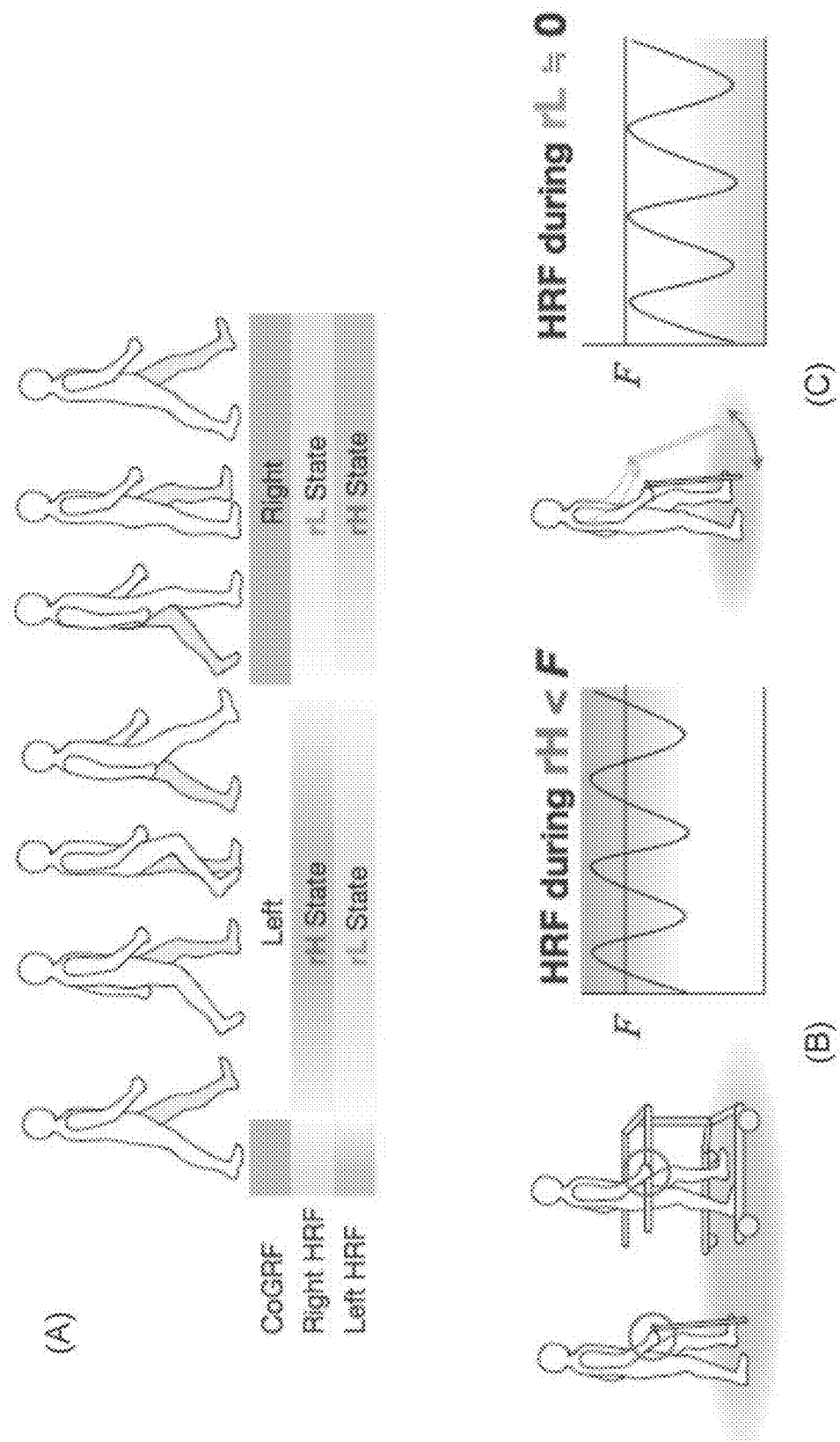
FIG. 7 is a conceptual diagram for explaining an rH state and an rL state of the handrail reaction force.

Therefore, as illustrated in FIG. 7A to FIG. 7C, the state where the handrail reaction force in the periodic increase/decrease becomes relatively high is defined as an rH (relatively High) state, while the state where the handrail reaction force in the periodic increase/decrease becomes relatively low is defined as an rL relatively Low) state.

In order to realize the walking using a highly-stable assistive tool represented by the walking training machine 2, the handrail reaction force in the rH state is required to be lower than the maximum support force by the upper limb muscles. On the other hand, in order to realize the walking using a less-stable assistive tool represented by a cane, the handrail reaction force in the rL state is further required to decrease to approximately 0N. Finally, in order to realize the walking without depending on the upper limbs, the handrail reaction force in both the rH state and the rL state is required to decrease to approximately 0N.

Accordingly, the concept of the rH state and the rL state of the handrail reaction force is essential for evaluating the process of improvements of the independent walking function and it is necessary to calculate the evaluation index for the handrail reaction force in each state.

Figure 8:
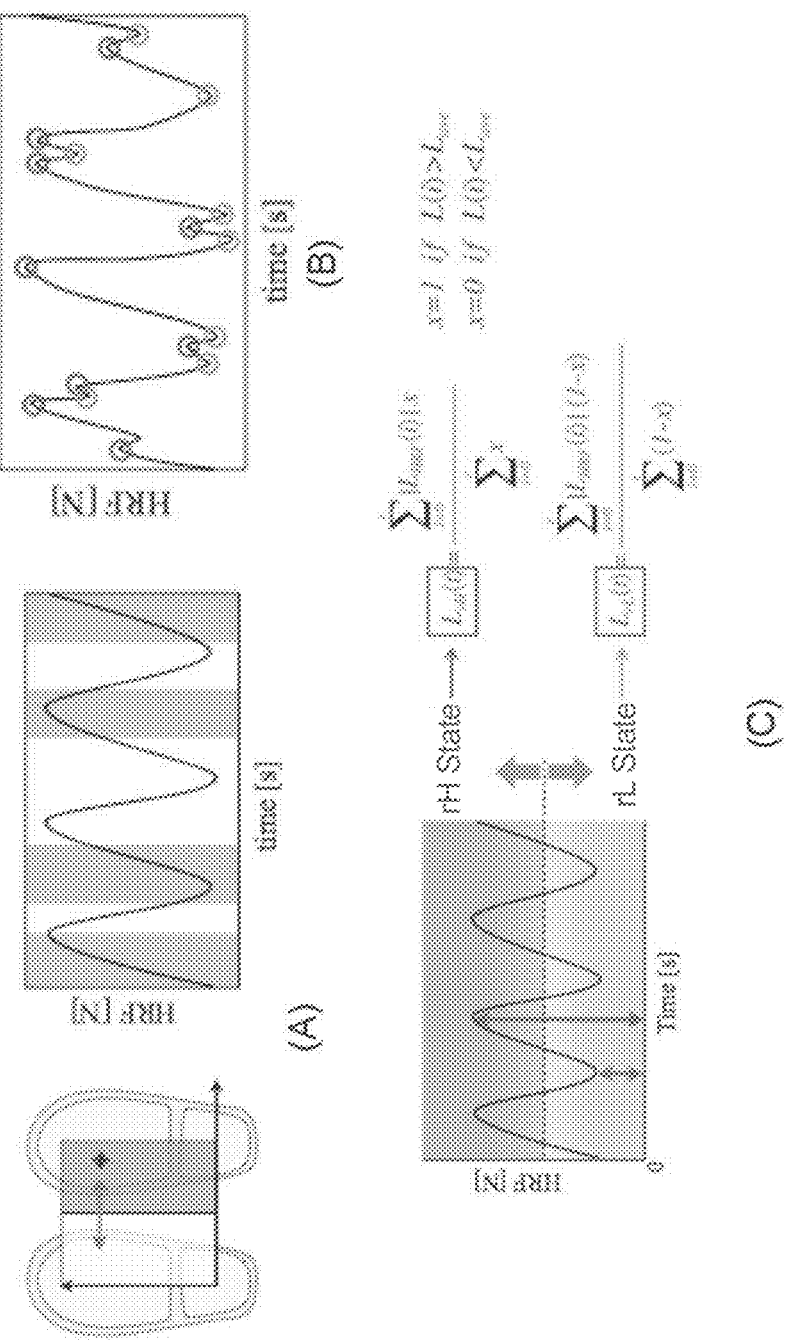
FIG. 8 is a conceptual diagram illustrating a method for calculating an evaluation index with respect to the handrail reaction force in the rH state and the rL state.

The following three types of calculation methods are possible as the method for calculating the evaluation index for the handrail reaction force in the rH state and the rL state: a first possible method is a calculation method based on the timing for switching the center of ground reaction force (CoGRF) between the right and the left (FIG. 8A); a second possible method is a calculation method based on a maximum point and a minimum point of the handrail reaction force value (FIG. 8B); and a third possible method is a calculation method based on a predetermined threshold value (FIG. 8C).

Regarding the first calculation method illustrated in FIG. 8A, a case can be assumed in which a phase difference may occur between the timing for switching the center of ground reaction force between the right and the left and the increase/decrease of the handrail reaction force, so that the evaluation index calculated by this method is inappropriate. Furthermore, the second calculation method illustrated in FIG. 8B is inappropriate for the HRF data showing multimodality in which the maximum and minimum values occur frequently. Therefore, the third calculation method illustrated in FIG. 8C is most reasonable and judges the rH state or the rL state of the handrail reaction force based on the threshold value.

Since the size of the handrail reaction force varies depending on the degree of seriousness of the lower limb functional disorder, the threshold value is set as an average value of the HRF data during walking with respect to each subject P. Time mean values FrH and FrL of the handrail reaction force in each state are set with respect to the handrail reaction force in the judged rH state and rL state and are defined as evaluation indexes which characterize the handrail reaction force of the lower limb functionally handicapped person.

(1-5-3) Method for Setting Handrail Reaction Force Map (HRFMAP)

A handrail reaction force map (HRFMAP) is set as a quantitative evaluation method with respect to improvements of the independent walking function by reducing the dependency on the upper limbs.

Figure 9:
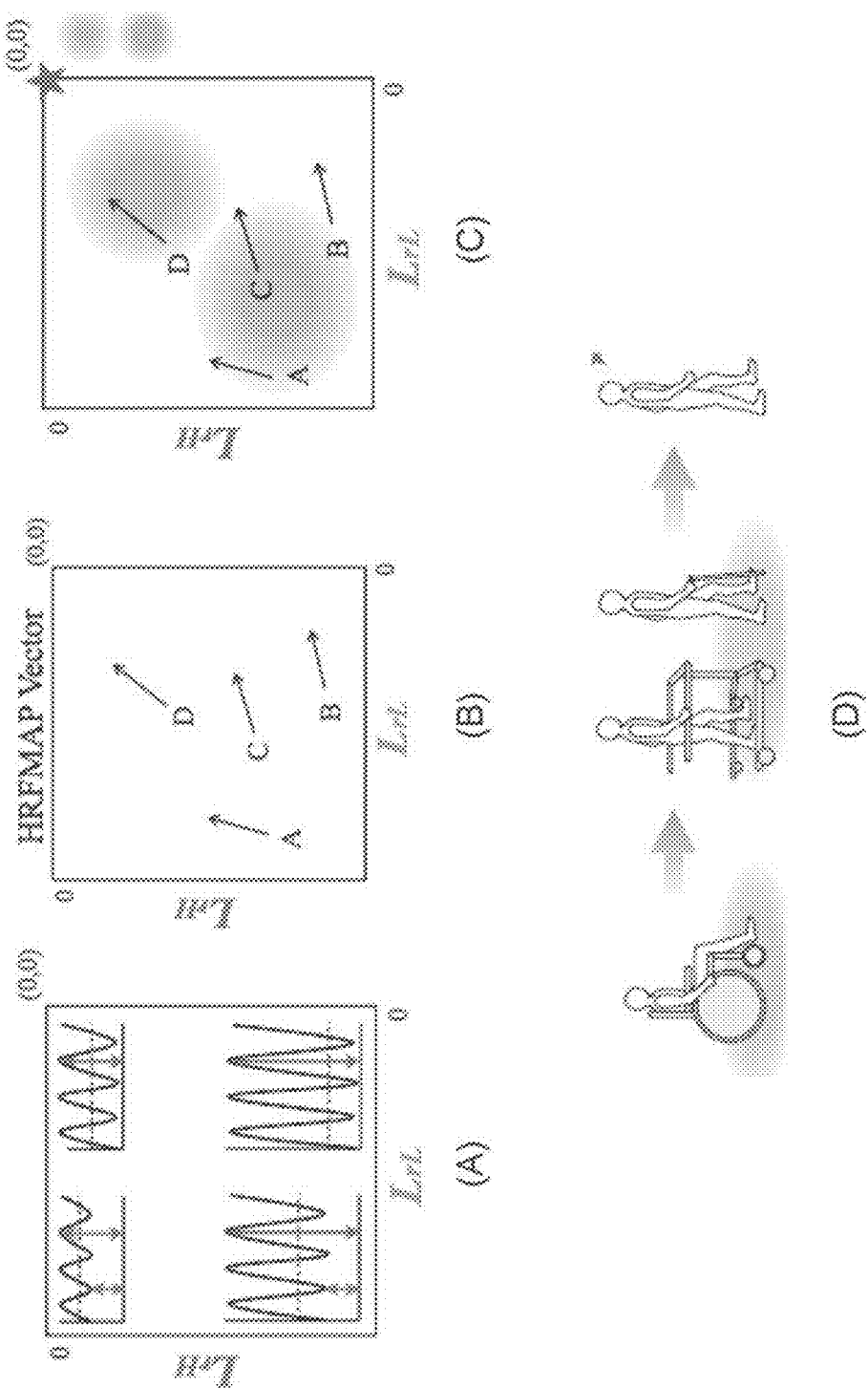
FIG. 9 is an explanatory diagram regarding generation of a handrail reaction force map.

The handrail reaction force map is a graph as illustrated in FIG. 9A to FIG. 9C where the horizontal axis represents the time mean value FrL of the handrail reaction force in the rL state and the vertical axis represents the time mean value FrH of the handrail reaction force in the rH state; and the origin (0, 0) is located at the upper right corner.

The handrail reaction force in synchronization with temporal changes in the gravity center position of the right and left foot sole surfaces of the relevant subject P based on the HRF data and the FRF data obtained during the walking training of the subject P is represented by a dot on the handrail reaction force map; and the subject P can understand the tendency of the handrail reaction force in the rH state or the rL state by visually checking the position of the dot.

Furthermore, changes in the handrail reaction force are represented as a vector on the handrail reaction force map; and the subject P can understand the tendency of reductions of the handrail reaction force from qualitative and quantitative points of view by visually checking the direction and length of the vector.

Accordingly, if the subject P visually checks the handrail reaction force map displayed on the display unit, they can visually check the process of improvements of the independent walking function as changes in the vector whose starting point is the handrail reaction force value, and the differences between the respective subjects P can be easily evaluated (FIG. 9B).

When the subject P having the lower limb functional disorder tries to improve the independent walking function and if the tendency of reductions of the handrail reaction force and the relevance between the handrail reaction force value and the independent walking function are clarified, not only such clarification can contribute to enhancement of the motivation of the subject P, but also such clarified data can be utilized as diagnostic materials for doctors.

So, in order to implement quantitative evaluation of the independent walking function, subjects P having the lower limb functional disorder are divided into a group using a wheelchair on a daily basis (a wheelchair group) and a group using an assistive tool (an assistive tool group), and a measurement test is conducted for the purpose of checking differences in distribution of both groups on the handrail reaction force map (FIG. 9C and FIG. 9D).

This measurement test is to measure the handrail reaction force of the subject P by performing a 10-m walking test and the subject P tries to reduce the handrail reaction force without using the visual feedback system. As a result of the measurement test, it was confirmed that dots (handrail reaction force values) corresponding to the results of the assistive tool group are concentrated in an upper right area of the handrail reaction force map, while dots (handrail reaction force values) corresponding to the results of the wheelchair group are dispersed in the entire handrail reaction force map.

Incidentally, since reductions of the handrail reaction force on both the right and left sides are required to improve the independent walking function, replotting processing was executed only either one of the right and left sides whose handrail reaction force values were higher with respect to the results of all the subjects P. As a result of calculating, for example, differences in standardized average values with respect to the replotted handrail reaction force map, it was verified that both the time mean values FrH and FrL of the handrail reaction force had large average value differences and tend to be significantly different from each other with respect to both the wheelchair group and the assistive tool group.

Therefore, the differences between the wheelchair group and the assistive tool group can be reflected in the handrail reaction force map, so that judgment analysis based on the Mahalanobis distance which makes it possible to consider differences between distribution and correlation coefficients is applied in order to clearly visualize differences in distribution of the both groups in the handrail reaction force map.

Figure 10:
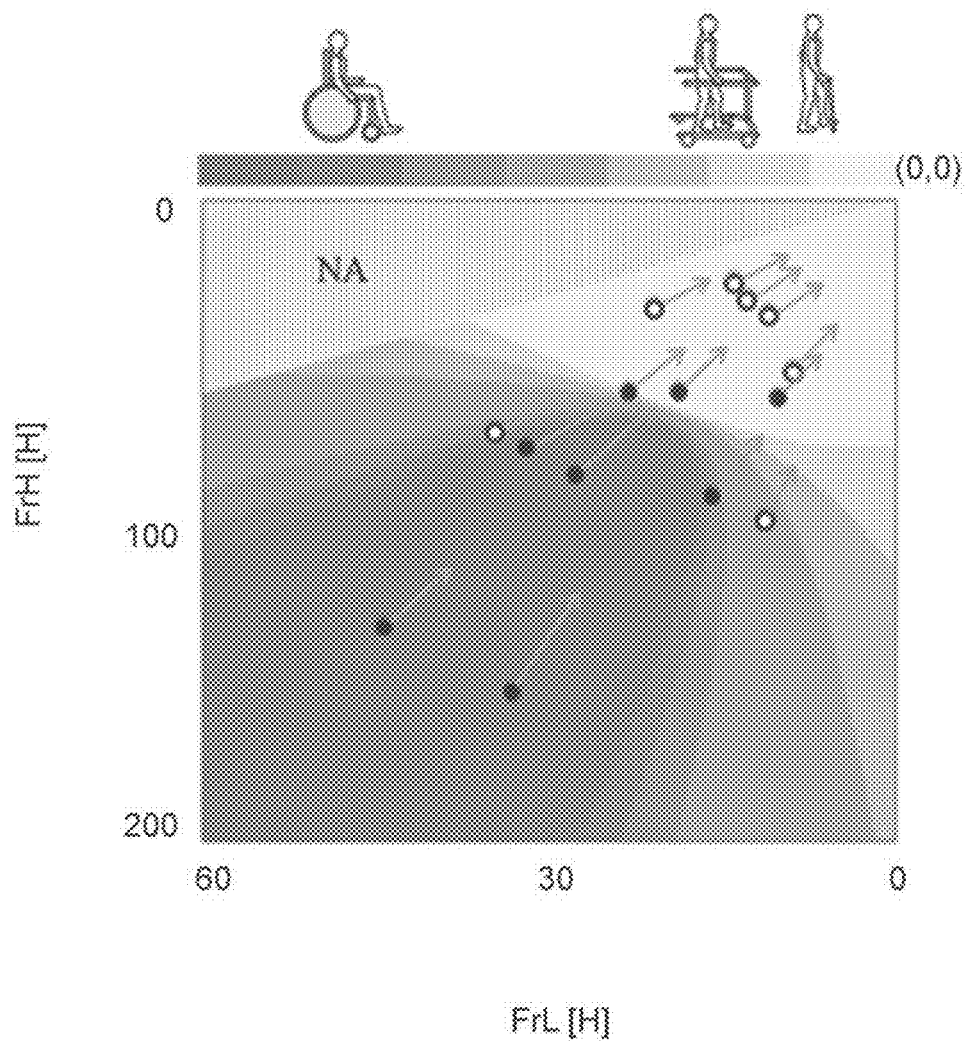
FIG. 10 is an explanatory diagram illustrating a handrail reaction force map in which a distribution tendency of symptom groups of a lower limb functional disorder.
Figure 11:
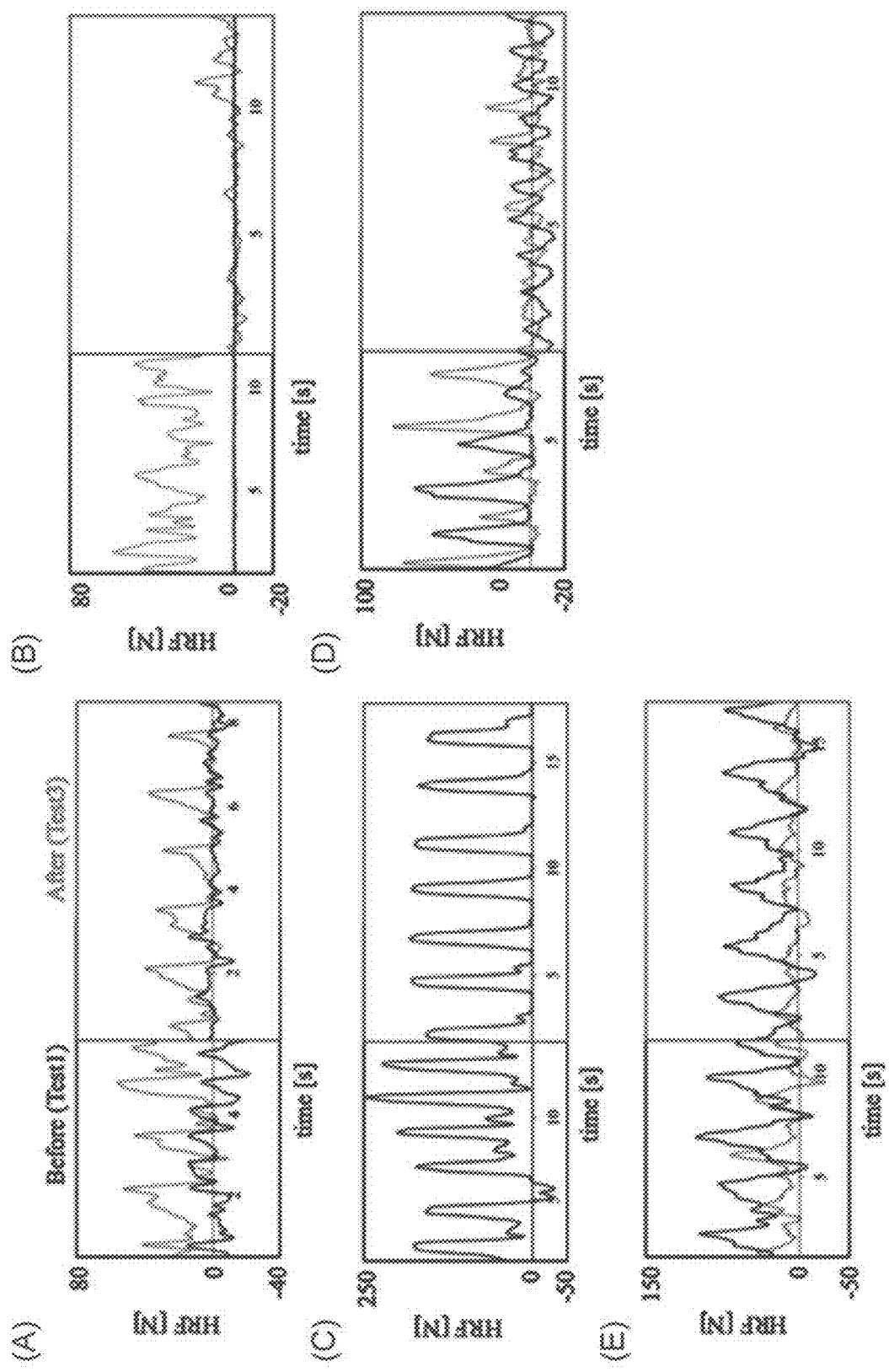
FIG. 11 shows time series graphs indicating changes in the handrail reaction force before and after intervention of a visual feedback system.

The Mahalanobis distance is calculated from both the wheelchair group and the assistive tool group with respect to all the dots (handrail reaction force values) on the handrail reaction force map, thereby adjusting grayscale and applying different colors in a phased manner according to a ratio of the calculated distance as illustrated in FIG. 10. As a result, the tendency of distribution of both the groups on the handrail reaction force map can be visualized and displayed.

By setting the handrail reaction force map as the evaluation index for evaluating the independent walking function as described above, it becomes possible to understand the progress of improvements of the independent walking function and set a clear target to reduce the handrail reaction force, and to contribute to proper diagnosis based on the quantitative results and enhancement of the motivation of the subject P having the lower limb functional disorder.

(1-5-4) Motor Learning Promoting Method by Visual Feedback System

In order to promote reductions of the handrail reaction force during the walking training to improve the independent walking function, it is necessary to recognize the handrail reaction force quantitatively by using the visual feedback system.

Performance information (hereinafter referred to as KP [Knowledge of Performance]) and result information (hereinafter referred to as KR [Knowledge of Result]) are generally utilized as information to be recognized by the subject P for motor learning.

The performance information KP is information about the motion itself and serves a role to link to the sense of the subject P by presenting whether the handrail reaction force is either in the rH state or in the rL state and how high/low the handrail reaction force value is.

The result information KR: is information about whether the handrail reaction force has achieved the target or not; and provides the subject with information about errors which are essential to have a feedback controller in the central nervous system (CNS: Central Nervous System) in the brain perform correction motions with respect to the walking motion.

The result information KP can be presented by presenting the right and left handrail reaction forces on a real-time basis. Regarding this result information KR, the target motion is continuous motion of walking, so that it is necessary to have transitional changes from the start of the motion reflected in the index.

Accordingly, an average value Lave of the handrail reaction force values is extracted chronologically as the result information KR about the handrail reaction force and recognition of the result information KR by the subject P is promoted by making use of the average value Lave and the target value.

It is believed that by constructing the visual feedback system for visually presenting the performance information KP and the result information KR based on the above-described knowledge, the performance information KP and the result information KR about the handrail reaction force are recognized, feedback loops including the motor center system are formed between the subject and the system, and motor learning regarding the reductions of the handrail reaction force is promoted.

(1-5-5) Demonstration Test for Handrail Reaction Force Reduction Effect

Now, it will be verified that the visual feedback system for the walking support system 1 has the effect of reducing the handrail reaction force of the subject P having the lower limb functional disorder; and the effect of the walking support system will be further evaluated from the viewpoint of the handrail reaction force map HRFMAP.

The effect of reducing the handrail reaction force in a case of intervention of the visual feedback system as a study design of the demonstration test is verified by comparing the handrail reaction force before and after the intervention of the visual feedback system.

Under this circumstance, it is assumed that confounding factors, that is, self-healing of the symptom and habituation of the walking motion itself exist. So, it is necessary to consider influences of such confounding factors. Accordingly, the following standards for incorporating a subject P are set: firstly, the subject P has the lower limb functional disorder; secondly, the subject P can understand a screen presented by the visual feedback system; thirdly, the subject is in the maintenance stage; and fourthly, the subject P receives the walking training periodically.

The subject P who satisfies the above-described incorporation standards performs a 10-m walking test for about 30 days to 40 days by using the walking training system and trying to reduce the handrail reaction force. For the first walking training, the 10-m test is performed ten times to find an average value. The visual feedback system is made to function while visually checking the handrail reaction force map in order to verify the effect of reducing the handrail reaction force by this walking training system.

Incidentally, as a result of performing the equivalent effect verification without using the visual feedback system, it was confirmed that there were less influences on the reductions of the handrail reaction force along with the elapse of time and the handrail reaction force value of the subject P having the lower limb functional disorder in the maintenance stage was steady.

On the other hand, when the effect verification was performed by using the visual feedback system, the handrail reaction force reduced significantly as the effect with intervention of the visual feedback system; and therefore, it was successfully confirmed that the visual feedback system is an essential factor for constructing an internal model in CNS for motor learning. The effect with the intervention of this visual feedback system did not extinguish but continued even for subsequent non-intervention training and it was confirmed that the post-intervention effect could also be achieved.

As a result of the above, it has been successfully verified that the subject P having the lower limb functional disorder can have the effect of reducing the handrail reaction force by using the visual feedback system by the walking training system.

Practically, FIG. 11A to FIG. 11E show the evaluation results of changes in the handrail reaction force before and after the intervention of the visual feedback system by using time series graphs. Referring to FIG. 11A to FIG. 11E, it can be confirmed that the subject P having the lower limb functional disorder reduced the handrail reaction force in both the rH state and the rL state, regardless of the degree of their functional disorder.

Furthermore, it can be confirmed with the handrail reaction force map that in the case of the non-intervention of the visual feedback system, directions of vectors are completely irregular; and in the case of the intervention of the visual feedback system, the directions of all the vectors become closer to the origin (0, 0) (rising to the right).

Figure 12:
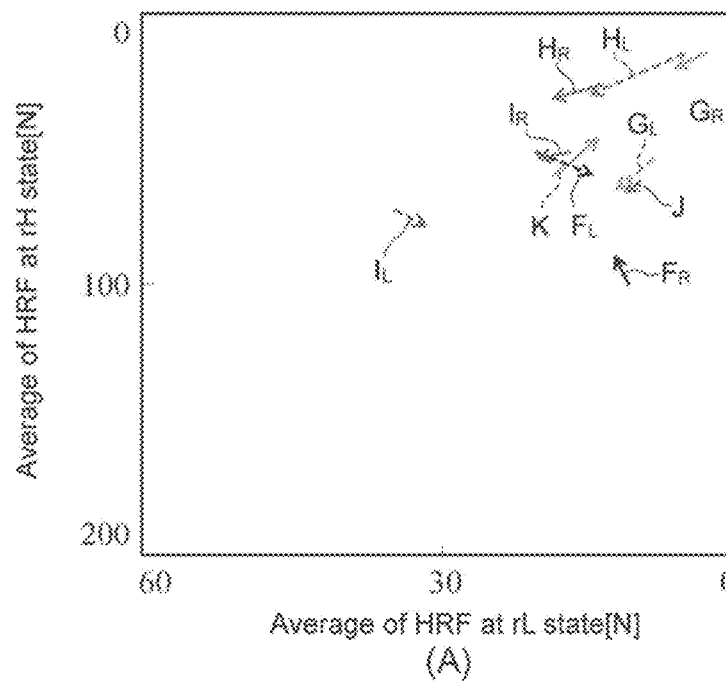
FIG. 12 is a diagram for explaining effect verification at the time of non-intervention of the visual feedback system.
Figure 12:
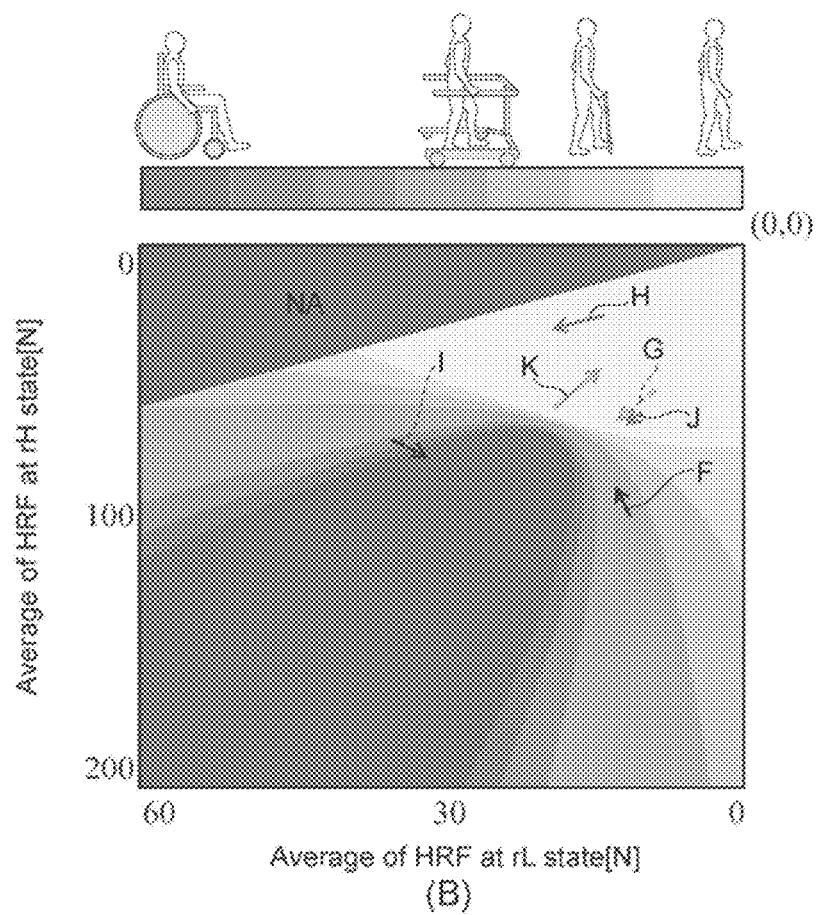
Figure 13:
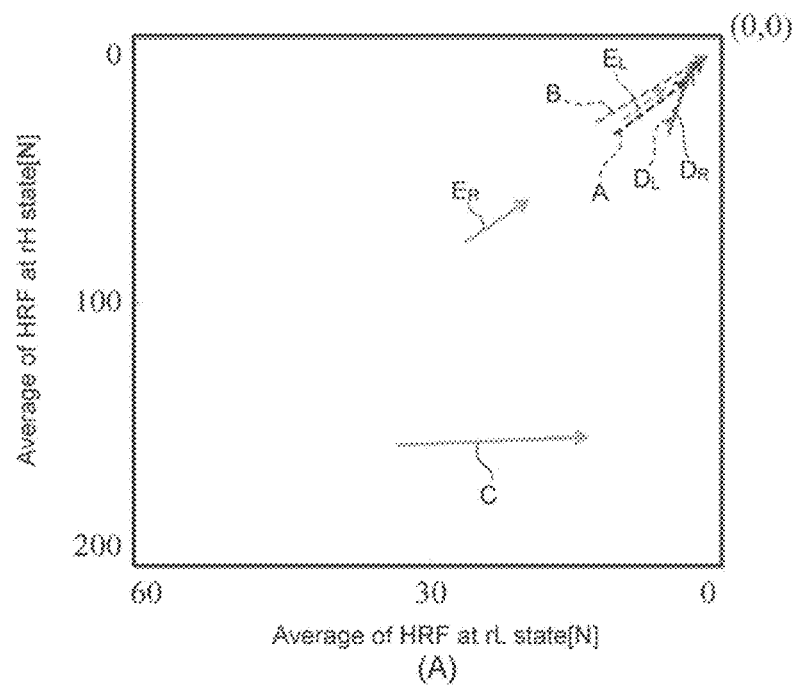
FIG. 13 is a diagram for explaining effect verification at the time of intervention of the visual feedback system.
Figure 13:
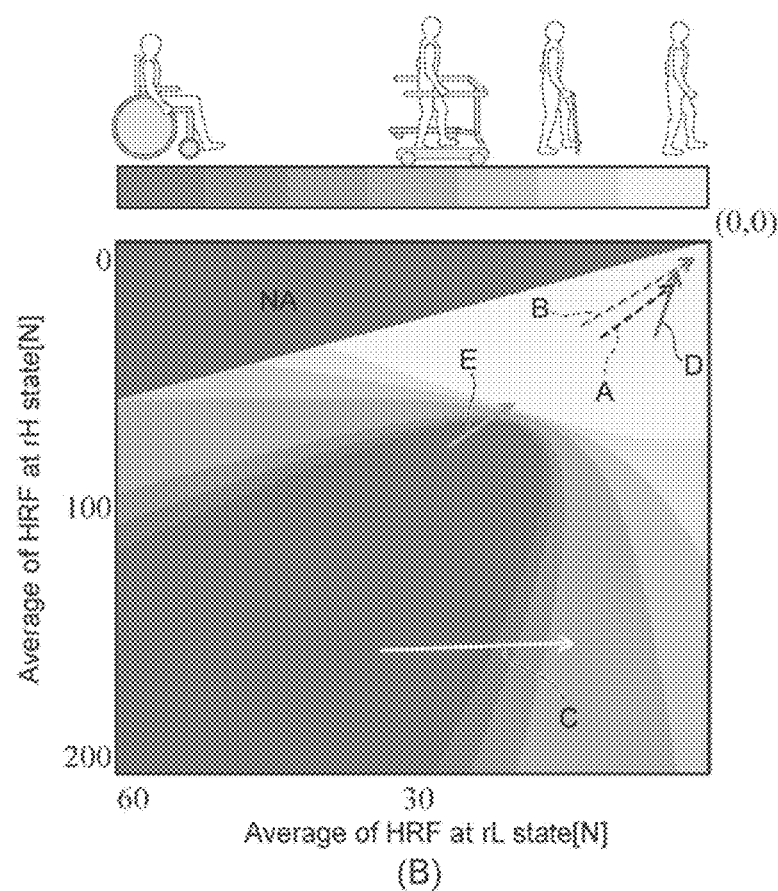

Regarding the demonstration test results of the 10-m walking test for 30 days using this handrail reaction force map, changes in the handrail reaction force by six subjects (F to K) at the time of non-intervention of the visual feedback system are displayed with vectors in coordinate systems in FIG. 12A and FIG. 12B; and changes in the handrail reaction force by five subjects (A to E) at the time of intervention of the visual feedback system are displayed with vectors in coordinate systems in FIG. 13A and FIG. 13B. Each vector is displayed as an arrow; and a solid line corresponds to the right hand and a broken line corresponds to the left hand.

It can be seen from FIG. 12A and FIG. 12B that according to the demonstration test results by the six subjects (F to K), the directions of the vectors in the handrail reaction force map are completely irregular. On the other hand, it can be seen from FIG. 13A and FIG. 13B that according to the demonstration test results by the five subjects (A to E), the directions of all the vectors in the handrail reaction force map are rising to the right and become closer to the origin (0, 0). Furthermore, FIG. 13(B) shows that the vectors in the handrail reaction force map proceed from the wheelchair group towards the assistive tool group and further become closer to the independent walking (the origin); and, therefore, the effect of reducing the handrail reaction force with the intervention of the visual feedback system has been successfully verified.

As a result of performing the judgment analysis by means of the aforementioned Mahalanobis distance and applying different colors by using the grayscale in this handrail reaction force map, it has been confirmed that the vectors in the case of intervention of the visual feedback system proceed from the wheelchair group towards the assistive tool group and further become closer to the independent walking (the origin).

As a result of the above, it has been successfully verified by the handrail reaction force map that the visual feedback system in the walking training system 1 has the effect of reducing the handrail reaction force with the lower limb functional disorder.

Accordingly, the walking training system 1 in this embodiment can visualize transitional reductions of the handrail reaction force, which are the evaluation of the dependency on the upper limbs, as the handrail reaction force map in order to allow the subject having the lower limb functional disorder to regain safe and independent walking and remarkably enhance the effect of improving the independent walking function through the evaluation index via the visual feedback system.

Figure 14:
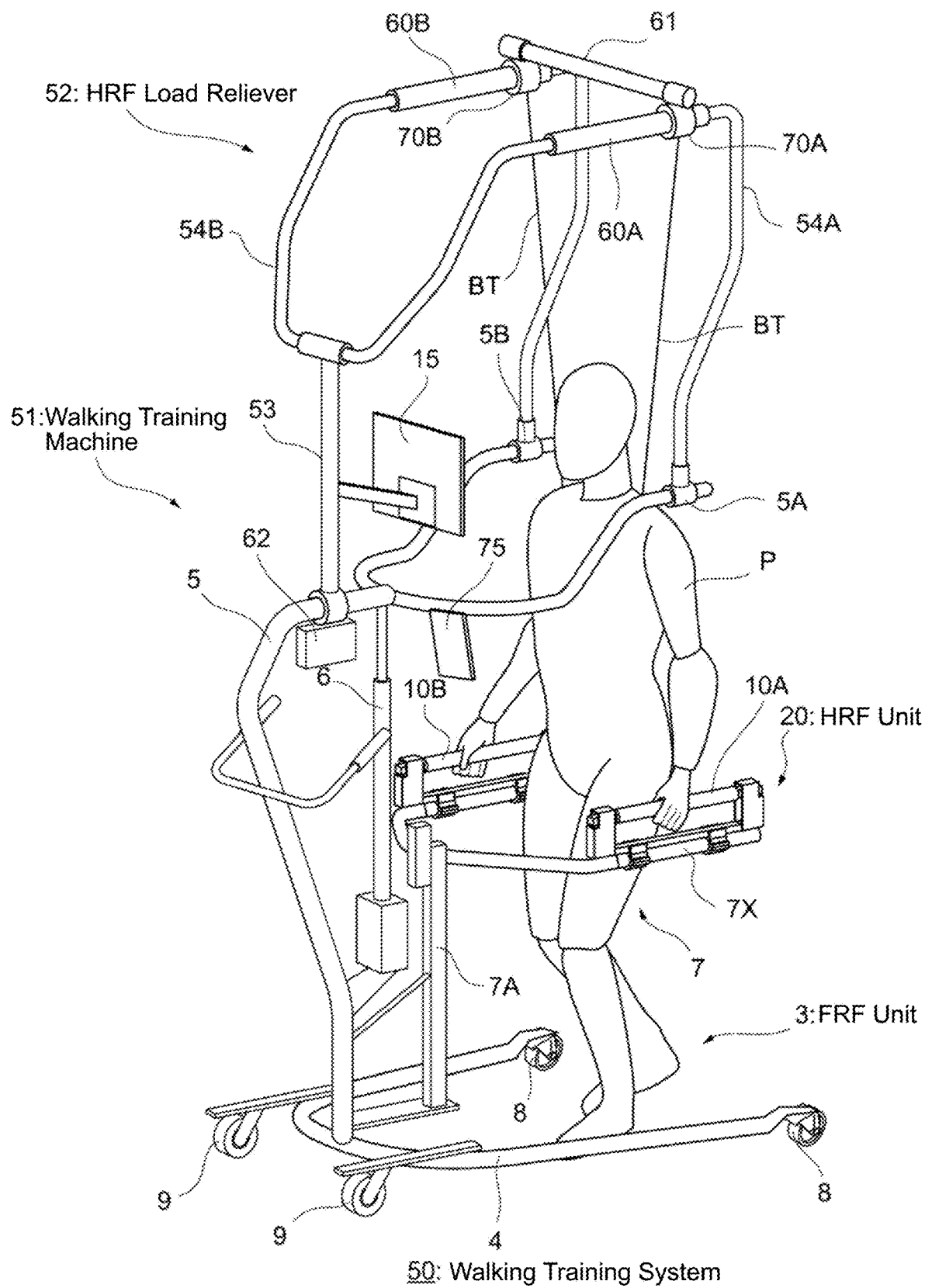
FIG. 14 is an overall view illustrating an appearance configuration of a walking training system to which a constant torque load relief is applied.

(2) Second Embodiment (2-1) Walking Training System to Which Constant Torque Load Relief Is Applied (2-1-1) Walking Training Machine Including HRF Load Reliever Referring to FIG. 14 in which the same reference numerals are assigned to parts corresponding to those in FIG. 1, an HRF load reliever (load relieving unit) 52 which constitutes a frame body surrounding the upper half of the body of the subject P from all directions is secured and mounted on a walking training machine 51 in a walking training system 50 from above the load relieving frame 5.

This HRF load reliever 52 includes a support pole 53 with its one end secured to the load relieving frame 5, and a pair of right and left lift frames 54A, 54B which extend from the other end of the support pole 53 so that their substantially V-shaped frames form arches; and the tips of the right and left lift frames 54A, 54B are secured and connected to the pair of tips of the U-shaped load relieving frame 5, respectively.

The right and left lift frames 54A, 54B have bilaterally symmetric frame shapes and the height of their upper part is set with reference to the load relieving frame 5 so that it becomes higher than the height of the subject P with various physical constitutions.

Uniaxial driving systems 60A, 60B are mounted at upper parts of both the right and left lift frames 54A, 54B for the HRF load reliever 52 and a sub-frame 61 is secured so as to link rear end regions of the respective uniaxial driving systems 60A, 60B in a crosswise direction.

A battery 62 is mounted at an end of the support pole 53 for the HRF load reliever 52 so as to supply electric power to each uniaxial driving system 60A, 60B.

Incidentally, with this walking training machine 51, unlike the walking training machine 2 illustrated in FIG. 1 described earlier, the wires are removed from the load relieving frame 5 and the display unit 15 is mounted at the center of the support pole 53.

The uniaxial driving system 60A, 60B mounted on each of the right and left lift frames 54A, 54B includes: a DC motor (not shown) as a driving source to receive the power supply from the battery 62; and a pulley 70A, 70B coupled integrally to an output axis of the DC motor.

Each of the pair of uniaxial driving system 60A, 60B has one end of a belt B secured to the pulley 70A, 70B and adjusts tension of the belt BT by winding or rewinding each belt BT. The other end of each of the belts BT is secured to the right or left end of a wearable harness to be mounted on the lower back part of the subject P.

Furthermore, the upper limbs supporting frame 7 is equipped with an operation unit 75 including an operation panel for inputting settings for all measurement function systems and driving systems of the walking training machine 51. The subject P can adjust the tension of the belt BT by means of the DC motor for the uniaxial driving system 60A, 60B by using this operation unit 75.

(2-1-2) Effect Verification of Visual Feedback System by HRF Load Reliever

With the walking training system 50 to which this walking training machine 51 is applied, the possibility to realize amplification of the effect of the visual feedback system is verified by using the HRF load reliever 52.

As a result of a demonstration test targeted at subjects P having the lower limb functional disorder in the maintenance stage, it was confirmed that in the case of intervention of the visual feedback system without using the HRF load reliever 52, a reduction of the handrail reaction force was immediately recognized with all the subjects P on the first day of the test, but there was a tendency of stagnation of the reduction effect on the second and third days of the test.

Regarding the walking training with the intervention of the visual feedback system, it is assumed that the effect of reducing the handrail reaction force can be further amplified if it is possible to enhance the physical support which will not hinder the independent walking function, the removal of psychological factors that cause anxiety when not depending on the upper limbs, and the sense feedback effect.

Therefore, the effect of reducing the handrail reaction force can be further amplified by activating the HRF load reliever 52 and causing the visual feedback system to intervene while relieving only a necessary amount of load at timing required by the subject P.

Specifically speaking, the following formula of the entire load relief amount F(t) is established where right and left handrail reaction force values are Lleft(t) and Lright(t), a moving average value of the handrail reaction force values is Lma(t), a target value is Lset(t), and furthermore a sensitivity adjustment value is G and an offset adjustment value is β.

[Math. 2]

$$F(t) = (L\text{left}(t) + L\text{right}(t)) \times G + (L\text{ma}(t) - L\text{set}(t)) \times \beta \quad (2)$$

Specifically speaking, regarding the entire load relief amount F(t), it becomes possible to relieve only the necessary weight in consideration of the sensitivity adjustment value G and the offset adjustment value β. It is desired that the load relief amount should be set according to the body weight of the subject P and the severity of the disorder.

(3) Other Embodiments

This embodiment has been described about the case where the walking training machine 2, 51 for the walking training system 1, 50 is applied to a walker with wheels, which moves along with the walking motion of the subject P as illustrated in FIG. 1 and FIG. 12; however, the present invention is not limited to this example and it is only necessary for the subject P to be able to use their own hands to support part of their body weight, so that variations of training methods suited for symptoms of the lower limb functional disorder of the subject P can be developed by applying the invention to various walking training machines such as a treadmill and a cane.

Figure 15:
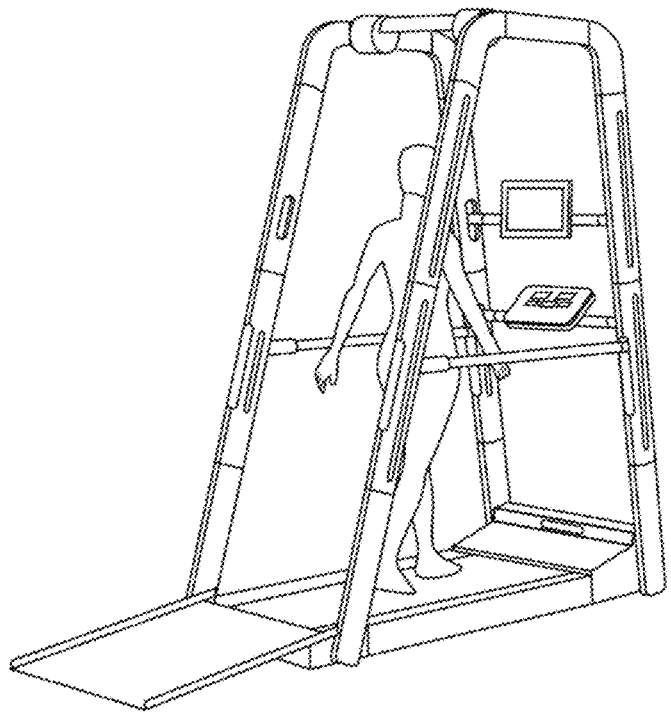
FIG. 15 is a perspective view illustrating an appearance configuration of a walking training system according to another embodiment.

For example, a walking training machine 70 as illustrated in FIG. 15 can have a rehabilitation effect of enhancing the activities of daily living (ADL: Activities of Daily Living) by performing the walking training to walk on a treadmill whose walking belt moves cyclically.

Moreover, when a cane (not shown) is used as the walking training machine, the subject P can rely on only one hand to bear part of their body weight; however, if the force applied to the cane is detected by the holding force detection unit, that will synchronize with the timing to switch the load applied to the gravity center of either one of the right and left foot sole surfaces and, therefore, the aforementioned evaluation index can be generated without any problem.

Furthermore, a movable robot (not shown) capable of autonomous travelling may be mounted in a front region of the base frame 4 for the walking training machine 1, 50 illustrated in FIG. 1 and FIG. 14 so as to support autonomous walking of the subject P. It is desired that the travelling status of the movable robot should be adjusted according to the state of reductions of the handrail reaction force, which is the evaluation of dependency on the upper limbs of the subject P.

Furthermore, this embodiment has been described about the case where the handrail reaction force map is given as the sense to the subject P in the visual feedback system; however, if image data representing this handrail reaction force map are wirelessly transmitted to an external server (not shown) and collected and accumulated for a long period of time and thereby used to analyze, for example, the tendency for each symptom of the lower limb functional disorder, it becomes possible to make an optimum diagnosis for each individual subject P. If the image data of the handrail reaction force map are treated as big data and managed and operated at the external server as described above, they can contribute to broad utilization such as establishment of an index regarding walking.

Furthermore, this embodiment has been described about the case where the sensory communication unit is configured of the control system unit 31 and the display unit 15 for the walking training machine 2 and feedback as the sense based on the evaluation index is applied to the visual feedback system which uses the display unit 15; however, the present invention is not limited to this example and a wide variety of sensory communication units can be applied if the feedback can be made as the sense to be felt which stimulate a human's five senses besides the visual sense of the subject P, for example, the auditory sense by means of sounds or the tactile sense by means of vibrations.

REFERENCE SIGNS LIST

1, 50 walking training system
2, 51, 70 walking training machine
3 FRF unit
4 base frame
5 load relieving frame
7 upper limbs supporting frame
7X, 7Y handrails
8, 9 wheels
10A, 10B holding parts
15 display unit
20 HRF unit
21F, 21R holding load detection units
24 mechanical force sensor
30 ground reaction force sensor
34, 40 control unit
52 HRF load reliever
60A, 60B uniaxial driving systems
P subject

The invention claimed is:
1. A walking training system comprising:
a ground reaction force sensor that is mounted on right and left foot sole surfaces of a subject and measures a load applied to each of the foot sole surfaces;
a gravity center position detecting sensor that detects a gravity center position of each of the right and left foot sole surfaces of the subject through a change in the load measured by the ground reaction force sensor;
a handrail that is mounted on a walking training machine for performing walking training and is held by the subject to support part of the subject's own body weight;
a mechanical force sensor that detects a force applied to both of a vertical downward direction and an opposite direction in a distribution of force acting on the handrail;
an MCU that generates an evaluation index for quantitatively reflecting transitional reductions of the force, which is applied to the handrail, on the basis of a relationship of periodically repeated increases and decreases of the force applied to the handrail and detected by the mechanical force sensor in synchronization with timing to switch the load, which is applied to the gravity center position of each of the subject's right and left foot sole surfaces and detected by the gravity center position detecting sensor, between right and left; and
a sensory communication transmitter that feeds back and transmits a transmission signal according to the evaluation index as a sense to the subject;
wherein the MCU:
divides the force applied to the handrail of the subject into a relatively large state, which is indicative of a first subject position having the handrail substantially supporting the subject and a relatively small state, which is indicative of a second subject position having the handrail minimally supporting the subject, the MCU dividing the force applied based on a predetermined threshold value and then forms a coordinate system by setting time mean values of the force in the relatively large state and the force in the relatively small state as respective orthogonal axes;

sets a state in which force applied to the handrail in the first subject position and the force applied to the handrail in the second subject position as an origin of the coordinate system and the origin of the coordinate system is set as a target value of an independent walking state and the MCU maps the transitional reductions of the force applied to the handrail as a vector representing a degree of recovery relative to the target value by setting a current state as a starting point; and generates the evaluation index by grouping a status of the subject's lower limb functional disorder according to a degree of seriousness and dividing each group in the coordinate system in a phased manner so that a distance from the target value becomes shorter in proportion to magnitude of dispersion and correlation of the vector.

2. The walking training system according to claim 1, comprising a frame body that relieves part of the body weight of the subject, wherein the frame body makes an adjustment to relieve only a predetermined amount, which is set with reference to the body weight of the subject, in synchronization with the timing to switch the load applied to the gravity center position of each of the subjects right and left foot sole surfaces between the right and the left.

3. The walking training system according to claim 1, further comprising an acceleration sensor that is mounted on the right and left foot sole surfaces of the subject and detects acceleration of each foot, wherein a degree of changes in a walking pattern of the subject is detected by continuing recording a detected result of the acceleration sensor for a predetermined period of time.

4. A walking training apparatus comprising:
a handrail that is held by a subject to support part of the subject's own body weight during walking training;
a mechanical force sensor that detects a force applied to both of a vertical downward direction and an opposite direction in a distribution of force acting on the handrail;
a receiver that externally receives data representing a gravity center position of each of right and left foot sole surfaces of the subject;
an MCU that generates an evaluation index for quantitatively reflecting transitional reductions of the force, which is applied to the handrail, on the basis of a relationship of periodically repeated increases and decreases of the force applied to the handrail and detected by the mechanical force sensor in synchronization with timing to switch the load, which is applied to the gravity center position of each of the subject's right and left foot sole surfaces based on the data received by the receiver, between right and left; and
a sensory communication transmitter that feeds back and transmits a transmission signal according to the evaluation index as a sense to the subject
wherein the MCU:
divides the force applied to the handrail of the subject into a relatively large state, which is indicative of a first subject position having the handrail substantially supporting the subject and a relatively small state, which is indicative of a second subject position having the handrail minimally supporting the subject, the MCU dividing the force applied based on a predetermined threshold value and then forms a coordinate system by setting time mean values of the force in the relatively large state and the force in the relatively small state as respective orthogonal axes;

sets a state in which force applied to the handrail in the first subject position and the force applied to the handrail in the second subject position as an origin of the coordinate system and the origin of the coordinate system is set as a target value of an independent walking state and the MCU maps the transitional reductions of the force applied to the handrail as a vector representing a degree of recovery relative to the target value by setting a current state as a starting point; and generates the evaluation index by grouping a status of the subject's lower limb functional disorder according to a degree of seriousness and dividing each group in the coordinate system in a phased manner so that a distance from the target value becomes shorter in proportion to magnitude of dispersion and correlation of the vector.

5. The walking training apparatus according to claim 4, comprising a frame body that relieves part of the body weight of the subject, wherein the frame body makes an adjustment to relieve only a predetermined amount, which is set with reference to the body weight of the subject, in synchronization with the timing to switch the load applied to the gravity center position of each of the subjects right and left foot sole surfaces between the right and the left.

* * * * *